US008383421B2

(12) United States Patent
Yanagida et al.

(10) Patent No.: US 8,383,421 B2
(45) Date of Patent: Feb. 26, 2013

(54) CARTRIDGE FOR AUTOMATIC MEASUREMENT AND MEASURING DEVICE USING THE SAME

(75) Inventors: Atsushi Yanagida, Tokyo (JP); Takashi Kurihara, Tokyo (JP); Hiroyuki Yokoi, Tokyo (JP); Atsushi Koyata, Tokyo (JP); Yoshikazu Okamura, Tokyo (JP); Daishi Miyamoto, Tokyo (JP)

(73) Assignee: Mitsubishi Chemical Medience Corporation, Tokyo (JP)

( * ) Notice: Subject to any disclaimer, the term of this patent is extended or adjusted under 35 U.S.C. 154(b) by 367 days.

(21) Appl. No.: 11/332,269

(22) Filed: Jan. 17, 2006

(65) Prior Publication Data

US 2006/0183217 A1    Aug. 17, 2006

Related U.S. Application Data

(63) Continuation of application No. PCT/JP2004/010308, filed on Jul. 20, 2004.

(30) Foreign Application Priority Data

Jul. 17, 2003    (JP) ................. 2003-198427

(51) Int. Cl.
*G01N 1/10*    (2006.01)
(52) U.S. Cl. ........ 436/180; 436/174; 436/807; 436/809; 435/288.1; 435/288.2; 435/288.3; 435/288.4; 435/288.5; 422/63
(58) Field of Classification Search ............ 422/63, 422/100, 102; 435/288.1, 288.2, 288.4, 288.3, 435/288.5; 436/171, 180, 807, 809
See application file for complete search history.

(56) References Cited

U.S. PATENT DOCUMENTS

| 4,950,457 | A | * | 8/1990 | Weick | 422/123 |
|---|---|---|---|---|---|
| 5,427,737 | A | * | 6/1995 | Glazer et al. | 422/26 |
| 5,605,665 | A | * | 2/1997 | Clark et al. | 422/102 |
| 5,787,146 | A | * | 7/1998 | Giebeler | 378/82 |
| 5,985,218 | A | * | 11/1999 | Goodale | 422/102 |
| 5,989,499 | A | * | 11/1999 | Catanzariti et al. | 422/63 |
| 6,100,079 | A | * | 8/2000 | Tajima | 435/239 |
| 6,337,053 | B1 | * | 1/2002 | Tajima | 422/102 |
| 6,357,583 | B1 | * | 3/2002 | Rainen | 206/205 |
| 6,509,193 | B1 | * | 1/2003 | Tajima | 436/49 |
| 2003/0157480 | A1 | * | 8/2003 | Smith et al. | 435/5 |
| 2004/0086429 | A1 | * | 5/2004 | Hiramatsu et al. | 422/102 |

FOREIGN PATENT DOCUMENTS

| EP | 1291654 B1 | 11/2006 |
|---|---|---|
| JP | 4-58158 | 2/1992 |
| JP | 11-500602 | 1/1999 |
| JP | 11-316226 | 11/1999 |

(Continued)

OTHER PUBLICATIONS

Office Action issued Aug. 18, 2011, in Chinese Patent Application No. 201010539070.6 (with English-language Translation).

*Primary Examiner* — Melanie J Yu
(74) *Attorney, Agent, or Firm* — Oblon, Spivak, McClelland, Maier & Neustadt, L.L.P.

(57) ABSTRACT

An object of the present invention is to provide a cartridge for automatic measurement used in an automatic measuring device, capable of automatically performing measurement including heat treatment of a sample, and a measuring device using the cartridge.
The present invention relates to a cartridge for use in measuring a component to be measured contained in a sample, comprising: at least a heat-treatment well for performing heat treatment of the sample; and a reaction well for reacting the component to be measured in the sample with a material specifically reacting therewith.

14 Claims, 4 Drawing Sheets

FOREIGN PATENT DOCUMENTS

| | | |
|---|---|---|
| JP | 2001-349896 | 12/2001 |
| JP | 2002-31643 | 1/2002 |
| WO | WO 97/05492 | 2/1997 |
| WO | WO 01/84152 | 11/2001 |
| WO | 02/08768 * | 1/2002 |
| WO | WO 02/08768 A1 | 1/2002 |

* cited by examiner

CARTRIDGE FOR AUTOMATIC MEASUREMENT AND MEASURING DEVICE USING THE SAME

TECHNICAL FIELD

The present invention relates to a cartridge for automatic measurement which is used by being incorporated in an automatic measuring device for automatically determining a component contained in a sample, and to an automatic measuring device using the cartridge for automatic measurement.

BACKGROUND ART

An analyzer for automatically analyzing human blood and the like, and a cartridge for automatic measurement used by being set in the analyzing apparatus have been proposed (JP 11-316226 A). This cartridge includes a reaction vessel for performing a reaction, and a plurality of storage vessels for which a reagent used for the reaction is filled. Furthermore, in order to cope with the difference in a dilution factor of a sample to be required depending upon an analyzing item, a cartridge provided with a diluting well for diluting a predetermined amount of a sample to a desired dilution factor has been proposed (International publication No. 01/84152).

When an analysis is performed using the above-mentioned automatic measuring device, pretreatment of a sample may be required depending upon an analyzing item. For example, in the case of measuring a virus antigen in the blood, usually, (1) the destruction of virus particles, (2) the exposure and extraction of a virus antigen, (3) the deactivation of an antibody to a virus antigen contained in a sample, and the like are required, and for these purposes, heat treatment is performed. The heat treatment is generally performed at a high temperature of 60° C. or higher. Therefore, in a conventional automatic measuring device having only a temperature controlling part suitable for an enzyme reaction and the like at about 37° C., pretreatment cannot be performed at a high temperature.

For the above reason, under present circumstances, it is necessary for the operator to perform heat treatment in advance to the sample using another heating device (heat block, etc.), and thereafter, the necessity of providing the sample to an automatic measuring device is needed, which takes a considerable amount of labor and time. Thus, such a procedure cannot be considered as complete automation even with the automatic measuring device. Furthermore, even when using an automatic measuring device capable of measuring a plurality of different items to be analyzed at the same time, an analyzing item requiring heat treatment needs to be handled separately, which results inconvenient.

DISCLOSURE OF THE INVENTION

It is an object of the present invention to provide a cartridge for automatic measurement used in an automatic measuring device, capable of automatically performing heat treatment of a sample, and a measuring device using the cartridge.

The inventors of the present invention found that a heat-treatment well for performing heat treatment of a sample is provided in a cartridge, and that the heat-treatment well is heated in an apparatus in which the cartridge is incorporated, whereby the analysis and the measurement of the sample, as well as the heat treatment can be automated, thereby achieving the present invention.

The present invention provides:
(1) A cartridge for use in measuring a component to be measured contained in a sample, characterized by comprising: at least a heat-treatment well for performing heat treatment of the sample; and a reaction well for reacting the component to be measured in the sample with a material specifically reacting therewith.

From another perspective of the present invention, there are provided:
(2) The cartridge according to (1), wherein the reaction between the component to be measured and the material specifically reacting therewith is an immunological reaction;
(3) The cartridge according to (1) or (2), further comprising a reagent-containing well for containing a reagent required for measurement, a dispensing well for dispensing the sample, a diluting well for diluting the sample, a washing well for washing a reaction product, and/or a measuring well for measuring the reaction product;
(4) The cartridge according to any one of (1) to (3), wherein each well is arranged linearly, and the heat-treatment well is placed at either end of the cartridge;
(5) The cartridge according to any one of (1) to (4), wherein a well not containing solution or material that is influenced by heating is placed adjacent to the heat-treatment well;
(6) The cartridge according to any one of (1) to (5), wherein the heat-treatment well is partitioned from a well placed adjacent thereto;
(7) The cartridge according to any one of (1) to (6), wherein a depth of a solution in a liquid form which influences a measurement value depending upon its capacity in the well is smaller than that of a diluting solution or a washing solution;
(8) The cartridge according to (7), wherein the solution which influences the measurement value depending upon its capacity in the well is a solution containing a material selected from the group consisting of a sample, a labeled antibody, and a magnetic particle;
(9) The cartridge according to any one of (1) to (8), wherein the information selected from the group consisting of information on a sample, information on an analyzing item, information on reagent management, and information on a calibration curve used for measurement is recorded on the cartridge;
(10) The cartridge according to (9), wherein the information is recorded with a bar code;
(11) The cartridge according to (9) or (10), wherein the record of the information is configured so as to be broken when the cartridge is used, whereby whether or not the cartridge has been used is determined;
(12) The cartridge according to any one of (1) to (11), wherein a calibration marking(s) showing an amount of a sample required for measurement is provided to the dispensing well;
(13) The cartridge according to any one of (1) to (12), wherein the cartridge is used by being incorporated in a measuring device including a cartridge-accommodating portion for accommodating the cartridge, a dispensing portion for dispensing a reagent and/or a sample to each well on the cartridge accommodated in the cartridge-accommodating portion, a measuring portion for measuring a reaction product on the cartridge accommodated in the cartridge-accommodating portion, and a temperature controlling portion capable of controlling at least the heat-treatment well and the reaction well of the cartridge to predetermined temperatures;
(14) The cartridge according to (13), wherein the heat-treatment well and the reaction well are controlled to desired temperatures different from each other, when the cartridge is incorporated in the measuring device; and

(15) The cartridge according to (13) or (14), wherein the heat-treatment well is arranged at an end of the cartridge, which is positioned on a back side of the measuring device, when the cartridge is set in the measuring device.

Further, the present invention provides:
(16) A measuring device comprising at least the cartridge-accommodating portion for accommodating the cartridge of any one of (1) to (15), a dispensing portion for dispensing a reagent and/or a sample to each well on the cartridge accommodated in the cartridge accommodating portion, a measuring portion for measuring a reaction product on the cartridge accommodated in the cartridge accommodating portion, and a temperature controlling portion capable of controlling at least the heat-treatment well and the reaction well of the cartridge to desired temperatures different from each other;
(17) The measuring device according to (16), wherein the temperature controlling portion is capable of controlling the heat-treatment well to 50° C. to 100° C. and the reaction well to 25° C. to 40° C.; and
(18) The measuring device according to (17), wherein the temperature controlling portion is composed of two heat blocks controlled separately.

BEST MODE FOR CARRYING OUT THE INVENTION

Figure 1:
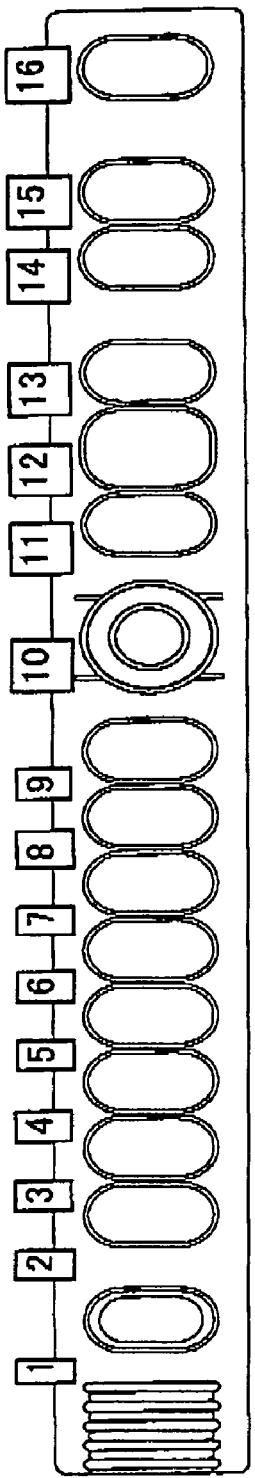
FIG. 1 Views showing one embodiment of a cartridge of the present invention. Part A represents a top view, and part B represents a cross-sectional view.
Figure 1:
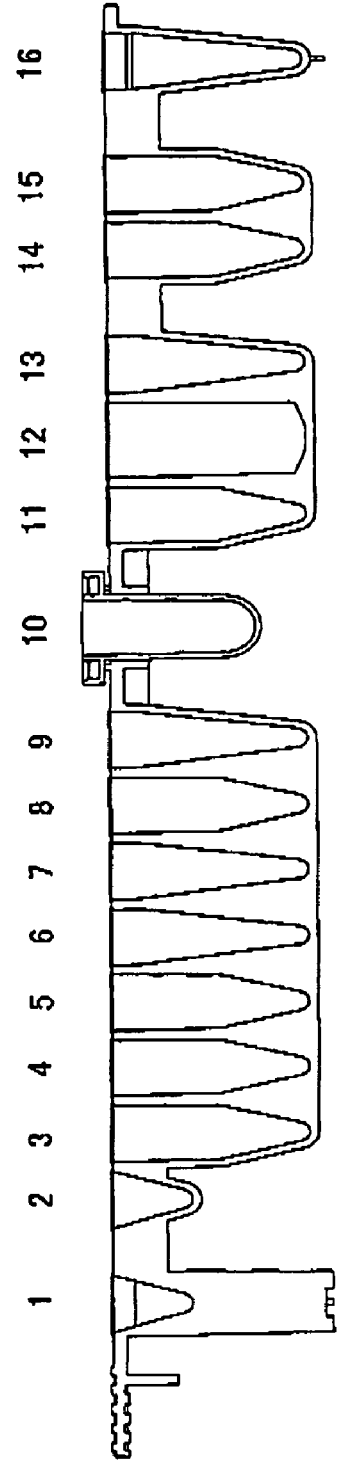

The terms used herein have the following meanings unless otherwise indicated specifically.

The cartridge of the present invention is used when a component to be measured contained in a sample is measured, and is usually used by being set in an automatic measuring device.

The above-mentioned measurement is performed usually by the method (hereinafter, which may be referred to as a "measuring method of the present invention") for measuring a component to be measured in a sample, including the steps of dispensing a sample containing a component to be measured, reacting the component to be measured contained in the sample with a substance that specifically reacts therewith, and measuring the amount of a reaction product. The measuring method of the present invention, typically, further includes the step of performing heat treatment of a sample. Also, preferably, the measuring method of the present invention further includes the step of diluting a sample.

The component to be measured (hereinafter, which may be referred to as an "analyzing item") is not particularly limited, and any component may be used as long as a substance specifically reacting with the component exists. Examples of a combination of a component to be measured and a substance that specifically reacts therewith include an antigen and an antibody, an antibody and an antigen, an enzyme and a substrate, and a sugar chain and a lectin. Thus, in the present invention, the expression "specifically reacts or specifically reacting" means biochemically and specifically binding. The component to be measured or the substance specifically reacting therewith may be a substance whose chemical nature may change between before and after the binding, such as substrates. Above all, for measurement of a component to be measured requiring heat treatment of a sample, the cartridge of the present invention is particularly suitable. An example of such a component to be measured includes a virus antigen, and specific examples thereof include a HCV core antigen and a Chlamydia antigen.

The sample may be any sample as long as it contains the above-mentioned component to be measured or has a possibility of containing it. Examples thereof may include blood, serum, plasma and urine. These samples may be heat-treated in the heat-treatment well, if required, depending upon the selected analyzing item. The presence/absence of heat treatment, heating temperature, heating time and the like, may be appropriately set in accordance with the selected analyzing item. For example, in the case of the above-mentioned HCV core antigen, heat treatment is performed, for example, at 65° C. for 30 minutes. In the case where it is considered that a sample after heat treatment has a high temperature, and may adversely influence in the well in which the sample is to be provided, the step of further cooling the sample appropriately may be performed (which also includes cooling by leaving the sample standing). However, in the case where the sample temperature does not cause any problem since the sample is mixed with a great amount of solution, e.g., in the case where the sample is diluted with a diluting well (described later), this step is unnecessary.

Conditions, etc. of the step of reacting the component to be measured and the substance which specifically reacts therewith, and the step of measuring the amount of the reaction product may be selected appropriately depending on the combination of the component to be measured and the substance which specifically reacts therewith. For example, the reaction of an enzyme and a substrate and measurement of the amount of a reaction product can be performed by mixing the enzyme with the substrate to allow the enzyme to act on the substrate and measuring the amount of the reaction product (degradation product of the substrate). The reaction of an antibody and an antigen and measurement of the amount of a reaction product can be performed by mixing the antibody or antigen with a solid phase carrier to which a corresponding antigen or antibody binds and a label to form a reaction product (immunocomplex), washing the reaction product to remove unreacted antibody or antigen and unreacted labeled compound from the immunocomplex (B/F separation), and measuring the amount of the label bound to the solid phase by the formation of the immunocomplex. Thus, in the present invention, the expression "measuring the amount of a reaction product" encompasses not only directly measuring the amount of a reaction product itself but also measuring the amount of a substance quantitatively related to the amount of the reaction product. From the thus-measured amount of the reaction product, the amount of the component to be measured in the sample can be calculated.

The cartridge of the present invention is characterized by including at least a heat-treatment well for performing heat treatment of a sample, and a reaction well for reacting a component to be measured in a sample with a substance that specifically reacts therewith. With such a configuration, even in the case where an analyzing item, requiring heat treatment of a sample, is selected, all the steps including heat treatment can be performed automatically.

In a preferable embodiment of the cartridge of the present invention, respective wells are aligned linearly. In this case, it is preferable that the heat-treatment well is placed at either end of the cartridge. Furthermore, it is preferable that a well not containing solution or substance that is influenced by heating is placed adjacent to the heat-treatment well. The well not containing solution or substance that is influenced by heating may be a well that is not used (since the cartridge of the present invention may be applicable to a number of kinds of items to be analyzed, a well that is not used may be present depending upon the analyzing item). Furthermore, the heat-treatment well may be partitioned from a well positioned adjacent thereto.

By configuring the cartridge as described above, when the heat-treatment well is heated, the influence of heat on a reagent and a reaction can be either reduced or prevented.

The cartridge of the present invention is usually used by being set in a measuring device that includes a cartridge accommodating portion for accommodating a cartridge, a dispensing portion for dispensing a reagent and/or a sample to each well on the cartridge contained in the cartridge accommodating portion, a measuring portion for measuring a reaction product on the cartridge contained in the cartridge accommodating portion, and a temperature controlling portion capable of controlling at least a heat-treatment well and a reaction well of the cartridge to a desired temperature. In a preferable embodiment of the cartridge of the present invention, when the cartridge is set in the measuring device, the heat-treatment well and the reaction well are respectively controlled by the temperature controlling portion of the measuring device. Usually, the heat-treatment well and the reaction well are controlled to different temperatures. However, in the case where a reaction temperature is high, the heat-treatment well and the reaction well may be controlled to the same temperature. Specifically, for example, the heat-treatment well is controlled to 50° C. to 100° C., preferably 60° C. to 70° C., and the reaction well is controlled to 25° C. to 40° C., preferably 33° C. to 38° C. These temperatures are appropriately set depending upon an intended analyzing item. The temperature of the heat-treatment well can be determined, for example, depending upon the presence/absence of heat treatment, heating temperature, heating time, and the like of an intended analyzing item. Furthermore, the temperature of the reaction well can be determined, for example, depending upon the conditions of the above-mentioned reaction step and the step of measuring the amount of a reaction product. It is preferable that the reaction well is placed away from the heat-treatment well so as not to be influenced by heat when the heat-treatment well is heated.

Furthermore, it is preferable that, when the cartridge is set in the measuring device, the heat-treatment well is placed at an end positioned on a back side of the measuring device. Specifically, in this embodiment, the cartridge of the present invention has a proximal end and a distal end in such a manner that, when the cartridge is set in the measuring device, the distal end is placed on a back side of the measuring device, compared with the proximal end, and the heat-treatment well is placed at the distal end of the cartridge. This makes it difficult for a person using the cartridge of the present invention to touch the heated heating well.

The cartridge of the present invention may further have a diluting well for diluting a predetermined amount of a sample to a desired factor. Regarding the measurement, depending upon the conditions such as the kind, concentration, measurement principle, and the like of the sample or the component to be measured, for example, an analysis method such as Enzyme Immunoassay (EIA method), Latex Immunoassay (LIA method), Turbidimetric Immunoassay (TIA method), Fluorescent Immunoassay (FIA method), or Chemiluminescent Enzyme Immunoassay (CLEIA method) is selected. Furthermore, depending upon the above condition, the sample may be measured in undiluted liquid, or the sample may need to be measured after being diluted. Furthermore, depending upon the condition, the dilution factor of the sample may vary. Even in such case, if a diluting well for diluting a predetermined amount of the sample to a desired factor is provided, an operator only dispenses a predetermined amount of the sample irrespective of the analyzing item in a measurement operation, and alleviates the labor of an operator required for confirming the dispensing amount, and greatly reduces the possibility of the failure of measurement due to the error of the dispensing amount. Furthermore, in the automatic measuring device in which the cartridge of the present invention is set, a mechanism for changing the dispensing amount of a sample depending upon an analyzing item is not required, so that the mechanism can be simplified. In the present invention, in the case where a diluting solution is not filled in the diluting well, when a diluting step is performed in the same way as in the analyzing item requiring dilution, it is apparent that the sample remains undiluted liquid (that is, the dilution factor is 1). Thus, the term "dilution" in the present specification is used to include retaining sample as undiluted liquid. Furthermore, in the case of diluting the sample at a high factor, it is preferable that at least two diluting wells are provided in the cartridge, and dilution is performed by at least two stages. The dilution factor of the sample and the diluting solution to be filled in the diluting well are selected appropriately depending upon the kind of a sample, a component to be measured, a substance that specifically reacts with a component to be measured, and the like. The diluting solution may contain a reagent required for pretreatment of a sample, and in this case, dilution and pretreatment are performed in the diluting well at the same time. The pretreatment includes treatment with an acid, an alkali, an organic solvent, a protein denaturing agent, an enzyme, and an inhibitor of a protease, treatment with a surfactant, and the like. A well containing pretreatment liquid may be provided separately from the diluting well.

Further, the cartridge of the present invention may have a reagent-containing well for containing a reagent necessary for the measurement of the component to be measured contained in the sample. The reagent-containing well may also serve as a reaction well. In other words, some of the reagents which participate in the reaction may be contained in a reaction well. The reagent to be contained in the reagent-containing well or the reaction well may include one species or a plurality of species as long as the contained reagents do not react with each other. The reagent to be contained may be liquid (for example, solution or suspension), or solid so far as it can be dissolved or suspended in the solution to be injected in the well.

Furthermore, it is preferable that the cartridge of the present invention further includes a dispensing well (hereinafter, which may be referred to as a "sample well") for dispensing a sample. Due to this, a predetermined amount can be added to the diluting well from the dispensing well in which the sample has been dispensed by a uniform process. Furthermore, when the sample is dispensed from a container in which the sample has been collected to a cartridge, it is not necessary to perform strict control of an amount, which makes the operation of an operator easy. Furthermore, in the automatic measuring device in which the cartridge of the present invention is to be set, it is not necessary to provide an additional mechanism such as a mechanism for directly quantifying and dispensing the sample from a master sample container outside the cartridge in order to dispense a predetermined amount to the cartridge, so the mechanisms can be simplified. Furthermore, if a calibration marking (s) showing the amount of the sample required for measurement is provided to the dispensing well, a required amount of the sample can be dispensed to the cartridge easily and exactly. The dispensing well may also function as a heat-treatment well.

Figure 2:
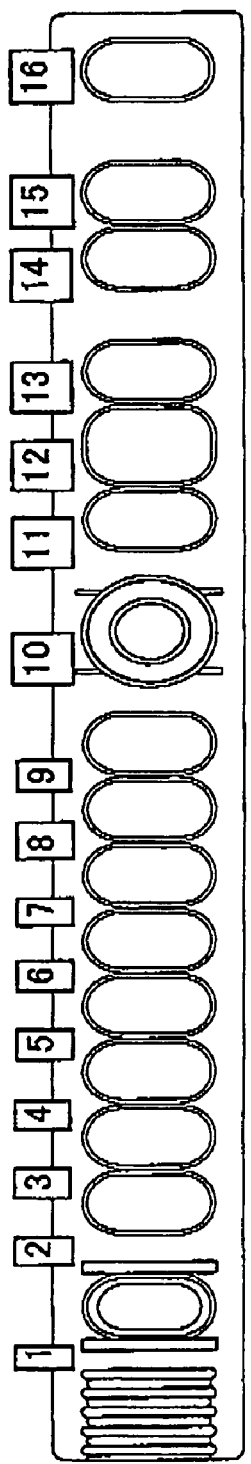
FIG. 2 Views showing another embodiment of the cartridge of the present invention. Part A represents a top view, and part B represents a cross-sectional view.
Figure 2:
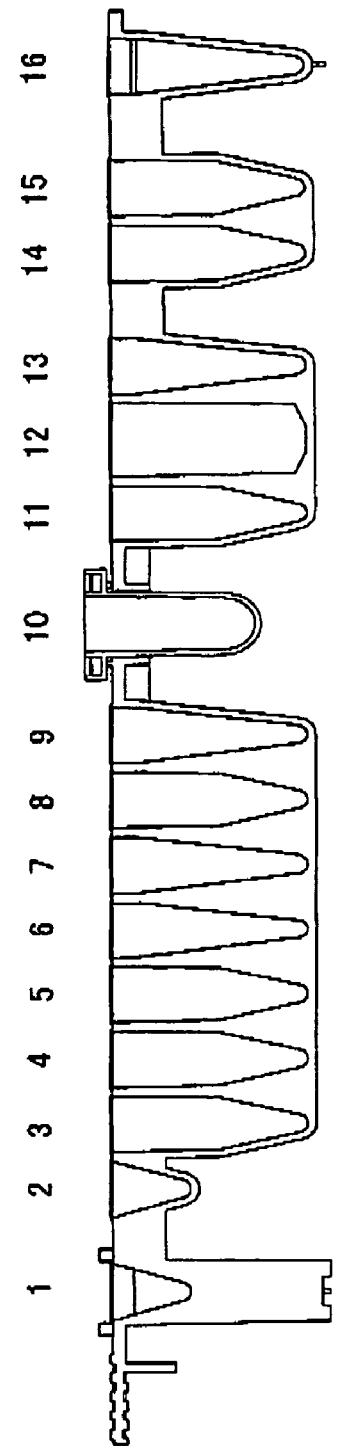

A wall may be provided around the dispensing well. This avoids the problems such as sample dispensed to the dispensing well leaks to touch the hand of an operator, the sample flows to another well, the sample adheres to an aluminum seal sealing the well, and a pipette tip for perforating the aluminum seal to cause contamination, and the like. The wall to be provided may be placed around the periphery of the well. For example, in the case where the dispensing well is placed on a side (the proximal end) closest to a handle portion at an end of the cartridge, a straight wall can also be provided between the handle portion and the dispensing well, and between the dispensing well and another adjacent well. The wall also can be provided independently, or is allowed to protrude continuously from the inner wall of the well. Since the possibility of the leakage of the dispensed sample can be reduced, it is preferable that the wall is formed so as to protrude continuously from the inner wall of the well. The wall can have, for example, a size of about 0.5 mm to 5 mm. FIG. 2 shows an example of the cartridge having such a dispensing well. In the cartridge, a sample well (1), a labeled antibody containing well (2), a washing well 5(3), a washing well 4(4), a washing well 3(5), a labeled antibody reaction well (6), a magnetic particle containing well (7), a washing well 1(8), a washing well 2(9), a photometric well (10), a diluting solution containing well 1(11), a diluting solution containing well 2 (12), a luminescent substrate containing well (13), a diluting well 1(14), a diluting well 2(15), and a heat-treatment well (16) are placed linearly in this order. Furthermore, the sample well (1) is provided with the wall.

The cartridge of the present invention may have a measuring well for measuring the amount of a reaction product. For example, a photometric well for optical measurement can be provided. Herein, for example, in the case where a special measurement condition is required (e.g., in the case where the measurement needs to be performed under a dark condition), the measuring well may be provided in another cartridge, or may be configured so as to be separable. For example, only the measuring well is composed of a material capable of blocking light, and combined with the cartridge, whereby a facility such as a darkroom is unnecessary.

The shape and size of the cartridge of the present invention are not particularly limited. However, for ease of handing for the operator, the cartridge is preferably of, for example, a boat form in which a reagent-containing well, a sample-dispensing well, a diluting well, a reaction well, and/or a measuring well are/is linearly arranged. A plurality of wells may be used for each type of well. Furthermore, for the measurement of a plurality of kinds of items to be analyzed, two or more lines of well groups necessary for measuring a component to be measured may be arranged in parallel. The material of the cartridge of the present invention is not particularly limited. However, in the case where a reagent or the like is sealed to be stored, a material having stability, which does not react with it, may be selected. Furthermore, in the case of performing heat treatment at a high temperature, a material excellent in heat resistance and heat conductivity may be selected.

In the cartridge of the present invention, the reaction between the component to be measured and the substance specifically reacting therewith are preferably an immunological reaction. That is, it is preferred that the component to be measured and the substance specifically reacting therewith are an antibody or an antigen.

As the immunological reaction, a method of reacting a sample, a first material immunologically and specifically reacting a component to be measured in the sample, and a second material specifically reacting a first immunocomplex generated by the reaction at a time (hereinafter, which may be referred to as a "one-step method"), and a method of reacting them in two stages (hereinafter, which may be referred to as a "two-step method") are known.

In the present invention, it is preferred to use the two-step method. Specifically, for example, a component to be measured in a sample is reacted with a substance immunologically and specifically reacting therewith to form a first immunocomplex and then the first immunocomplex is reacted with a label immunologically specifically reacting therewith to form a second immunocomplex. In this case, the cartridge of the present invention preferably has a reaction well for forming the first immunocomplex and a reaction well for forming the second immunocomplex. More preferably, the cartridge of the present invention has washing wells for B/F separation corresponding to the respective reaction wells. The washing wells may be filled with a washing solution in advance or filled by dispensing from, for example, another cartridge or bottle.

As such an immunological reaction, a method of performing B/F separation with a magnetic force in an aspirating/discharging line of liquid provided in a dispensing portion of an apparatus, using the first material immobilized at magnetic particles collectable with a magnetic force. Specifically, for example, a method of performing B/F separation by contacting a magnet from the outside to a pipette tip, a flexible tube, a stainless pipe, or the like used as a flow line for aspirating/discharging liquid from a well of the cartridge, and integrating magnetic particles on an inner wall surface thereof (e.g., U.S. Pat. No. 3,115,501), and the like are used.

The reagent and/or the solution necessary for the measurement of the component to be measured contained in a sample used in the present invention may be filled in another cartridge in advance and the cartridge may be used in combination with the cartridge of the present invention in performing measurement. Measurement can be performed, for example, by filling a diluting solution of a sample, a substance and a labeled compound specifically reacting with the component to be measured in the sample, and a washing solution for washing the immunocomplex in another cartridge, etc. in advance, and dispensing the reagent and/or the solution to the each well on the cartridge of the present invention by a uniform operation. By such a method, the mechanism of the instrument can be simplified and the structure of the cartridge of the present invention can be simplified and downsized. In addition, it becomes easy to solve the problem on the storage stability of the reagent and/or the solution to be used. Of course, it is possible to fill the reagents and/or solutions necessary for measurement into both of the cartridge of the present invention and the other cartridge and use them in combination.

All of the reagents and/or the solutions necessary for the measurement of the component to be measured contained in the sample may be filled in the cartridge of the present invention. It is preferred that all the necessary reagents, for example, a diluting solution of a sample, a substance and a labeled compound specifically reacting with the component to be measured in the sample, and a washing solution for washing the immunocomplex, etc. are filled in the cartridge of the present invention in advance. By so doing, all procedures for one component to be measured can be handled in one cartridge, so that wastes of reagents can be cut. Supply of water or discharge of water become unnecessary, leading to further simplification of the measuring device and to reduction in time required for the measurement.

In another preferable embodiment of the present invention, the depth of a solution in a liquid form influencing the measurement value depending upon its capacity in the well is set to be smaller than that of a diluting solution or a washing solution. Herein, the term "depth" refers to a distance from the bottom surface in the well to a liquid surface of the solution. In the device in which the cartridge of the present invention is to be set, a dispensing portion in which a pipette tip and the like can be mounted is provided, and liquid is injected to the well of the cartridge by the pipette tip, or aspirated from the well. At this time, when the depth of the solution influencing the measurement value depending upon its capacity in the well is large, the solution adheres to the outside of the pipette tip, and is brought to another well, which makes it impossible to perform exact measurement. The inventors of the present invention paid attention to this, and came up with the following idea: by setting the depth of the solution to be smaller than that of a diluting solution or a washing solution, even if the solution is brought to another well, the solution adhering to the pipette tip can be removed with the diluting solution or the washing solution when the pipette tip is inserted in the well containing the diluting solution or the washing solution. Furthermore, it is preferable that the depth of the well containing a solution influencing the measurement value depending upon its capacity in the well is set to be small in accordance with the depth of the solution. With such configuration, the loss caused by the adhesion of a trace amount solution to the well wall and the like are reduced, and measurement with a high precision can be performed. Examples of the solution influencing the measurement value depending upon its capacity in the well include a solution containing a sample, a labeled antibody, magnetic particles, or the like.

It is preferred that the cartridge of the present invention, when it is filled with, for example, reagents and/or solutions, and the like such as a diluting solution, a labeled compound, a washing solution, and the like in advance, is preferably sealed with an aluminum laminate foil, a plastic film or the like on its top in order to prevent contamination of foreign matter and evaporation/deterioration of reagents. Seals of aluminum laminate foil are particularly preferred since they can be easily opened automatically by a perforating mechanism in the automatic measuring device or by leading end of the pipette tip or the like. In the case where the reagent(s) and/or solution(s) and the like are filed in another cartridge and measurement is performed using the cartridge in combination, it is preferred that the cartridge is also sealed.

In another embodiment of the cartridge of the present invention, information, such as information on a sample, information on an analyzing item, reagent management information, and information on a calibration curve used for measurement are recorded on the cartridge. The information is recorded, for example, by printing or attaching a bar code to the cartridge. Furthermore, a magnetic recording means, an IC chip in which information is input, or the like may be attached. By providing a bar code or the like to the cartridge, for example, if an automatic measuring device that recognizes a bar code of the cartridge and automatically selects an analyzing item is used, an operator merely selects the cartridge, whereby an arbitrary analyzing item can be measured easily and efficiently by using one automatic measurement device. Furthermore, it is not necessary to operate a work sheet, which is a major cause of an error in setting of an analyzing item, as performed in a conventional usual automatic measurement apparatus, and a plurality of kinds of items to be analyzed can be measured easily without failure. Furthermore, storing and managing a reagent are also easily done. Furthermore, even if the operator does not input the information on a calibration curve in the automatic measuring device, the information on a calibration curve can be input automatically in the device. The record of the information such as the bar code is configured to be broken when the cartridge is used, whereby a used or unused cartridge can be determined. For example, when information is recorded on a seal for sealing the well, the seal is broken by a perforating mechanism of the automatic measuring device, a leading end of the pipette tip, or the like when in use, whereby the record breaks. Because of this, whether the cartridge has been used or unused can be determined automatically.

In the measuring method of the present invention, in the case where the sample contains a plural components to be measured, it is preferred to measure the plural components to be measured by using a plurality of cartridges or a cartridge in which two or more lines of well groups are arranged in parallel at the same time. In such a case, it is preferred that use be made of an automatic measuring device which is capable of measuring a plurality of items to be analyzed in parallel at the same time and in which a plurality of the cartridges of the present invention can be set, or an automatic measuring device in which the cartridge of the present invention having wells corresponding to a plurality of items to be analyzed (two or more lines of well groups being arranged in parallel) can be set in.

In the automatic device in which the cartridge or cartridges of the present invention are set when in use, known means may be used, respectively, such as, for means for aspirating a predetermined amount of liquid from one well and dispensing it to another well, means for mixing the content in the well, means for performing B/F separation, means for measuring the amount of a reaction product or of a labeled compound, means for calculating the amount of the component to be measured from the result of the measurement of the amount of the reaction product or of the labeled compound, means for controlling the temperature of a cartridge, means for recognizing a bar code, means for performing measurement of a plurality of cartridges at the same time, and so on.

Hereinafter, the present invention will be illustrated referring to an example of immunoassay, more particularly, chemiluminescent enzyme immunoassay (CLEIA), as one example of a preferred aspect.

A cartridge according to a preferred aspect is a cartridge for automatic measurement to be used by being set in an automatic measuring device that automatically quantitates a component to be measured in a sample. This cartridge has a reaction well for reacting the component to be measured with the substance immunologically specifically reacting therewith, a plurality of reagent-containing well for being filled with reagents, respectively, to be used in the reaction, a sample-dispensing well for dispensing a sample, a diluting well for diluting the sample, a heat-treatment well for heating the sample, a washing well for performing B/F separation, and/or a photometric well. As described above, the reagent-containing well may also serve as a reaction well. Preferably these wells are used as follows. The diluting well is filled with a diluting solution in an amount sufficient for diluting a predetermined amount of the sample to a desired dilution. A plurality of reagent-containing wells are individually filled with a solid phase carrier for carrying out immunologically specific reaction, a labeled antigen or antibody, a reagent for performing the measurement of the amount of the label, etc. The washing well is filled with a washing solution for washing immunocomplexes.

Further, in the reagent-containing well of the cartridge, for example, a solid carrier (sensitized solid phase) to which an antigen or antibody binds is placed, so that the well can also serve as a reaction well. The solid phase carrier may include polystyrene beads, magnetic particles and the like, which have been conventionally used in immunoassays. Furthermore, it is also possible that no solid phase carrier is added to the well but an antibody or antigen is used by being immobilized to the inner wall of the well.

The immunoassay to be used in the present aspect is preferably a chemiluminescent enzyme immunoassay (CLEIA) which is advantageous in respect of sensitivity. The solid phase carrier is preferably magnetic particles by which the B/F separation, which is essential to the CLEIA, can be easily performed by means of a magnet. The B/F separation can be performed by application of a magnetic field to the cartridge from outside thereof by use of a permanent magnet, an electromagnet or the like. Also, as disclosed in JP 11-262678 A, application of a magnetic field can be performed by utilizing a magnet provided on the aspiration and discharge sides of the pipette tip, etc., of the dispenser.

The other reagent-containing wells may also serve as a reaction well by adding thereto a labeled antigen or antibody. For example, examples of the labeled compound include enzymes, radioisotopes, coloring substances, fluorescent substances, and luminescent substances, various colored particles. In chemiluminescent enzyme immunoassays (CLEIA), enzymes are preferably used. Examples of such a labeling enzyme include alkaline phosphatase, peroxidase, galactosidase, and glucooxidase. As substrates for the labeling enzymes, those substrates which correspond to respective enzymes are suitably used. For example, adamantyl methoxyphenyl phosphoryl dioxetane (AMPPD) can be used for alkaline phosphatase, luminol/peroxide can be used for peroxidase, and adamantyl methoxyphenyl-$\beta$-D-galactosyldioxetane (AMPGD) can be used for galactosidase.

When using a diluting well, it is preferred that a predetermined amount of diluting solution for each item for analyzing is filled in advance in the diluting well. For example, in the case where two different items to be analyzed, i.e., hepatitis C virus (HCV) antibody and HBs antigen (HBsAg) are to be measured, both of the two items can be concurrently processed in the same analyzing step, by using two cartridges which have the same amount of sample, the same amount of reagent solution of solid phase carrier, the same amount of reagent solution of labeled antigen or antibody, the same amount of washing solution, and the same measuring conditions of labeled compound, etc. for the two items, but have different amount of the diluting solution filled in diluting wells for the two items in an automatic measuring device provided with two or more mechanisms for performing a series of immuno-reaction processes in parallel.

In the case where a high dilution of a sample is to be performed, it is preferred that two or more diluting wells are provided on the cartridge so as to perform two or more stages dilution be performed. FIGS. 1 and 2 illustrate examples of such cartridge.

Furthermore, as described above, the cartridge of the present invention and another cartridge filled with a reagent and/or a solution required for measurement can be used together for measurement. For example, the cartridge of the present invention having a dispensing well, a diluting well, a reaction well, a washing well, and a photometric well is used without being filled with a reagent and/or a solution. In contrast, a diluting solution, a solid-phase carrier, a labeled antigen or antibody, a reagent for measuring the amount of a labeled compound, and the like are filled in another cartridge, and they are dispensed from that cartridge to the cartridge of the present invention, whereby measurement can be performed similarly.

In the sample diluting step, pretreatment of a sample may be performed by adding an acid, an alkali, an organic solvent, a protein denaturant, a detergent, etc. to the diluting solution. For example, in the case where blood (whole blood) is used as a sample, it is preferred that the pretreatment is performed by adding any desired detergent, etc. since blood contains a large amount of interference and for some other reasons. By performing the dilution and pretreatment of the sample in this manner at the same time, high precision measurement can be easily performed even when blood and the like are used as samples. As a result, the present invention can be preferably used in emergency tests and point of care testing (POCT) to be performed by physicians and nurses.

The washing solution for the washing off of unreacted sample and labeled compound from immunocomplexes (B/F separation) requires much expense in time and effort for preparing the washing solution, supplementing it during measurement and disposal of waste liquid when the washing solution is supplied from a part of devices in the automatic measuring device as seen in the conventional automatic measuring device. Further, the washing solution used in the conventional automatic measuring device standardized with respect to the composition and liquid amount of the washing solution regardless of items to be analyzed, so that it is impossible to adopt optimal composition of the washing solution for each item for analyzing. From the aforementioned points, it is preferred that the washing solution is also contained in a cartridge. However, in the case where, for example, the composition or the liquid amount is identical, the washing solution may be uniformly supplied from a part of devices in the automatic measuring device as described above.

For example, in an enzyme chemiluminescence method, the measurement of a labeled compound can be performed by mixing an immunocomplex with a substrate of a marker enzyme, and thereafter, measuring the labeled compound directly from the photometric well with a photomultiplier tube or the like. For example, in the case of using a combination of a measuring well composed of a material capable of blocking light with the cartridge, measurement is performed by bringing an end of the photomultiplier tube in direct contact with an upper part of the well, whereby measurement can be performed easily with a high precision even in the absence of a facility such as a darkroom. Furthermore, in the case of the enzyme immunoassay, an immunocomplex is mixed with an enzyme substrate solution, and thereafter measurement light with a measurement wavelength is irradiated from a bottom part or a side part of a measurement well to measure light transmitted through the measurement well.

The automatic measuring device of the present invention includes at least a cartridge accommodating portion for accommodating the cartridge of the present invention, a dispensing portion for dispensing a reagent and/or a sample to each well on the cartridge contained in the cartridge accommodating portion, a measuring portion for measuring a reaction product on the cartridge contained in the cartridge accommodating portion, and a temperature controlling portion for controlling at least the heat-treatment well and the reaction well in the cartridge to predetermined temperatures different from each other.

The cartridge-accommodating section may be the same as a conventional cartridge-accommodating section except that it is made to have a structure capable of accommodating the cartridge of the present invention. The dispensing section is constituted by conventional mechanisms such as liquid aspirating/discharging mechanisms, etc. corresponding to the kinds and properties of a reagent and/or a sample. The term "dispensing" as used herein encompasses both of the following: transferring a reagent and/or a sample from one well to another well on a cartridge, and transferring a reagent and/or a sample from outside a cartridge to a well on the cartridge. The measuring section is constituted by conventional mechanisms such as photometric mechanisms depending on the kinds and properties of a reaction product. In the case where the measurement is performed by using the cartridge of the present invention having provided thereon two or more lines of well groups in parallel or a plurality of the cartridges of the present invention, the automatic measuring device is preferably an device having provided in parallel therein a plurality of mechanisms for performing a series of immuno-reactions and capable of operating and controlling the processes at the same time of, for example, dispensing a sample, diluting the sample, dispensing a reagent, B/F separation and photometry. In this manner, even in the case of immunoassays, a plurality of items to be analyzed can be measured at the same time by using an device which performs only a single style of analyzing process without substantially increasing time required for measurement even for different items to be analyzed.

It is preferable that a portion (pipette tip, etc.) of the dispensing part, which comes into contact with a reagent and/or a sample, can be replaced. By replacing this portion for each measurement, preventing the contamination of a cartridge to be used for the subsequent measurement becomes easy. Furthermore, as described above, it is further preferred that B/F separation using a magnetic force is performed in the pipette tip or the like.

The temperature controlling part controls at least the heat-treatment well and the reaction well to predetermined temperatures different from each other. Specifically, for example, the temperature controlling part controls the heat-treatment well to 50° C. to 100° C., and the reaction well to 25° C. to 40° C. In a preferable embodiment, the temperature controlling part is composed of two heat blocks which are controlled separately.

Furthermore, as described above, it is preferred that a bar code or the like is provided to the cartridge of the present invention, and measurement is performed using a device having a mechanism of recognizing the bar code. By using a device capable of recognizing a bar code and automatically selecting an analyzing item, for example, it is unnecessary to separately set whether or not heat treatment should be performed, the reaction temperature, and the photometric condition; the analysis of measurement results can be performed easily; the operator's input of information on a calibration curve is unnecessary; and the like. Thus, the automatic measurement can be performed further easily and efficiently. More specifically, all the measurement steps can be performed automatically merely by the operator's selection of a cartridge corresponding to an intended analyzing item, whereby measurement can be performed exactly with reduction of human-induced mistakes.

EXAMPLE

Hereinafter, the present invention will be illustrated in more detail by way of examples. However, the following examples are merely for illustration and the scope of the present invention should not be construed as being limited by the following examples. It is obvious to one skilled in the art that any variations, improvements or modifications can be made to the present invention without departing from the spirit of the present invention.

Example 1

Cartridge for Two-Stage Reaction

FIG. 1 shows an example of the cartridge of the present invention. In this cartridge, a sample well (1), a labeled antibody containing well (2), a washing well 5(3), a washing well 4(4), a washing well 3(5), a labeled antibody reaction well (6), a magnetic particle containing well (7), a washing well 1(8), a washing well 2(9), a photometric well (10), a diluting solution containing well 1(11), a diluting solution containing well 2(12), a luminescent substrate containing well (13), a diluting well 1(14), a diluting well 2(15), and a heat-treatment well (16) are arranged in the stated order linearly. This cartridge is sealed with an aluminum foil in an upper part, and an analyzing item is recorded by a bar code on the aluminum foil.

Figure 3:
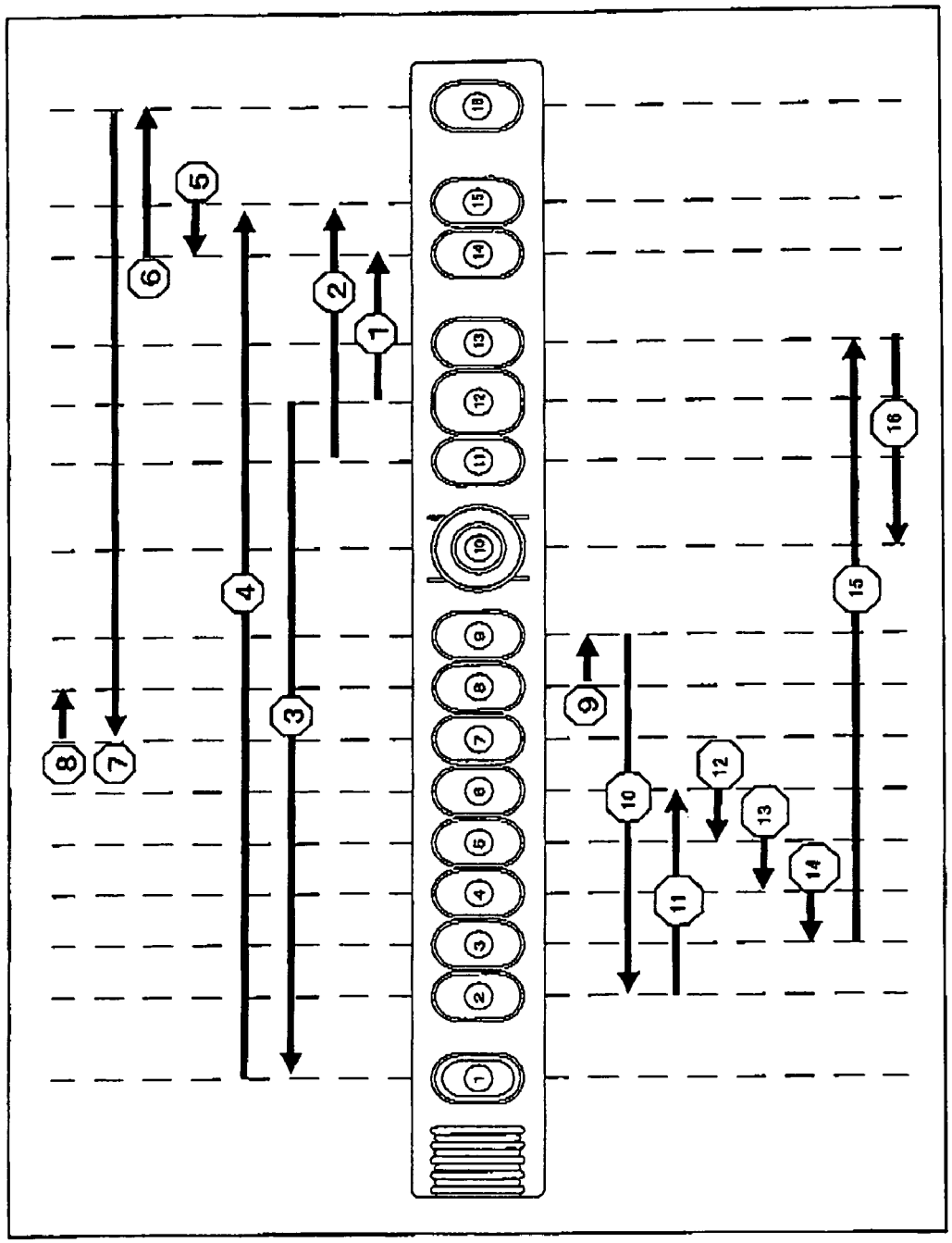
FIG. 3 A diagram showing an example of the movement of a solution in measurement using the cartridge of the present invention.

The operation in the case of performing measurement using the above-mentioned cartridge, using an automatic measuring device provided with a 6-set aspirating/discharging mechanism and magnetic particle separating mechanism, will be described (FIG. 3). In this example, after a sample is reacted with magnetic particles bound by an antibody specifically reacting with a component to be measured, a reactant and a labeled antibody are reacted with each other (two-step method). Furthermore, this example includes the step of performing heat treatment of a sample. In FIG. 3, arrows represent the movement of a solution, and numbers on the arrows represent the order of the movement of a solution.

1. A sample is dispensed to a sample well (1).
2. A reagent cartridge in which the sample has been dispensed is set in an automatic measuring device. At most, six reagent cartridges can be set simultaneously. Cartridges may be used for measuring items to be analyzed different from each other, and arranged in an arbitrary manner.
3. The automatic measuring device is started.
4. The automatic measuring device reads a bar code attached to the reagent cartridge, and recognizes which analyzing item has been selected.
5. A diluting solution is aspirated from the diluting solution containing well 2(12), and the entire amount is discharged to the diluting well 1(14). Furthermore, a diluting solution is aspirated from the diluting solution containing well 1(11), and the entire amount is discharged to the diluting well 2(15).
6. A diluting solution is aspirated from the diluting solution containing well 2(12), and then, a sample is aspirated from the sample well (1). The entire amount is discharged to be mixed in the diluting well 2(15), whereby a first-stage diluting step is performed.
7. The sample diluted in the first stage is aspirated from the diluting well 2(15), and the entire amount is discharged to be mixed in the diluting well 1(14), whereby a second-stage diluting step is performed.
8. The sample diluted in the second stage is aspirated from the diluting well 1(14), and the entire amount is discharged to the heat-treatment well (16), whereby heat treatment is performed at a desired temperature for a predetermined time.
9. The sample is aspirated from the heat-treatment well (16), and discharged in the magnetic particle containing well (7) to be mixed with magnetic particles, whereby the sample is allowed to react with the magnetic particles for a predetermined time.
10. After the reaction, the sample is aspirated from the magnetic particle containing well (7), and the magnetic particles are separated with a permanent magnet in a pipette tip where the sample has been aspirated (the magnetic particles are adsorbed to a pipette tip inner wall, and the solution is discharged), and moved to the washing well 1(8). After the magnetic particles are washed, the magnetic particles are separated with a permanent magnet, and moved to the washing well 2(9). The magnetic particles are washed again similarly, and the magnetic particles are separated with a permanent magnet.

11. A labeled antibody solution is aspirated from the labeled antibody containing well (2) under the condition that the magnetic particles are adsorbed to the pipette tip inner wall, and is discharged to the labeled antibody reaction well (6) together with the magnetic particles to be mixed with each other, they are allowed to react with each other for a predetermined time.

12. After the reaction, the sample is aspirated from the labeled antibody reaction well (6), and the magnetic particles are separated with a permanent magnet in a pipette tip where the sample has been aspirated, and moved to the washing well 3(5). After washing, the magnetic particles are further separated with a permanent magnet, and moved to the washing well 4(4). Furthermore, after washing, the magnetic particles are separated with a permanent magnet, and moved to the washing well 5(3) The magnetic particles are further washed, and separated with a permanent magnet.

13. A luminescent substrate is aspirated from the luminescent substrate containing well (13) under the condition that the magnetic particles are adsorbed to a pipette tip inner wall, and discharged to the photometric well (10) together with the magnetic particles so as to be mixed with a luminescent substrate solution. After the reaction for a predetermined time, the luminescent amount is measured with a photomultiplier tube (PMT) from an upper part of the photometric well (10).

Example 2

Figure 4:
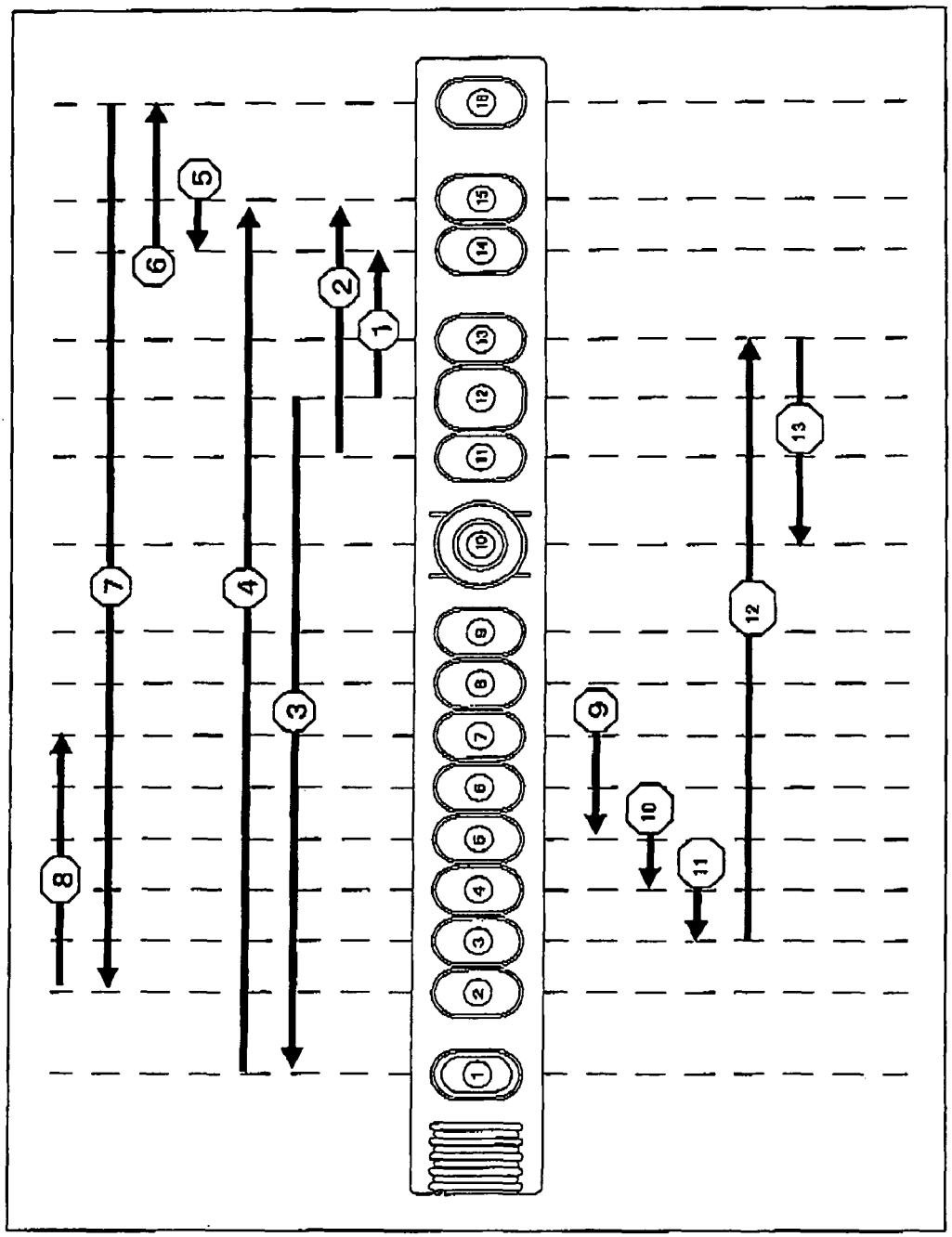
FIG. 4 A diagram showing another example of the movement of a solution in measurement using the cartridge of the present invention.

Another example of performing measurement using the cartridge described in Example 1 will be shown (FIG. 4). In this example, measurement is performed using the same device as that in Example 1, except that a sample, magnetic particles, and a labeled antibody are reacted with each other at the same time (1 step method). In FIG. 4, arrows represent the movement of a solution, and the number on the arrows represent the order of the movement of a solution.

1. A sample is dispensed to a sample well (1)
2. A reagent cartridge in which the sample has been dispensed is set in an automatic measuring device. At most, six reagent cartridges can be set simultaneously. Cartridges may be used for measuring items to be analyzed different from each other, and arranged in an arbitrary manner.
3. The automatic measuring device is started.
4. The automatic measuring device reads a bar code attached to the reagent cartridge, and recognizes which analyzing item has been selected.
5. A diluting solution is aspirated from the diluting solution containing well 2(12), and the entire amount is discharged to the diluting well 1(14). Furthermore, a diluting solution is aspirated from the diluting solution containing well 1(11), and the entire amount is discharged to the diluting well 2(15).
6. A diluting solution is aspirated from the diluting solution containing well 2(12), and then, a sample is aspirated from the sample well (1). The entire amount is discharged to be mixed in the diluting well 2(15), whereby a first-stage diluting step is performed.

7. The sample is aspirated from the diluting well 2(15), and the entire amount is discharged to be mixed in the diluting well 1(14), whereby a second-stage diluting step is performed.
8. The sample is aspirated from the diluting well 1(14), and the entire amount is discharged to the heat-treatment well (16), whereby heat treatment is performed at a desired temperature for a predetermined time.
9. The sample is aspirated from the heat-treatment well (16), and then, a labeled antibody solution is aspirated from the labeled antibody containing well (2) and discharged to the magnetic particle containing well (7) to be mixed with magnetic particles allowing to react for a predetermined time.
10. After the reaction, the sample is aspirated from the magnetic particle containing well (7), and the magnetic particles are separated with a permanent magnet in a pipette tip in which the sample has been aspirated (the magnetic particles are adsorbed to a pipette tip inner wall, and a solution is discharged), and moved to the washing well 3(5). After the magnetic particles are washed, the magnetic particles are separated again with a permanent magnet, and moved to the washing well 4(4). The magnetic particles are washed similarly, and separated with a permanent magnet to be moved to the washing well 5(3). The magnetic particles are washed further, and separated with a permanent magnet.
11. A luminescent substrate is aspirated from the luminescent substrate containing well (13) under the condition that the magnetic particles are adsorbed to a pipette tip inner wall, and discharged to the photometric well (10) together with the magnetic particles to be mixed with a luminescent substrate solution. After the reaction for a predetermined time, the luminescent amount is measured with a photomultiplier tube (PMT) from an upper part of the photometric well (10).

INDUSTRIAL APPLICABILITY

According to the present invention, measurement including heat treatment of a sample can be performed automatically, using a automatic measuring device and a cartridge for automatic measurement used for the same. Furthermore, in a preferred embodiment of the cartridge of the present invention, a sample can be heated without influencing the reaction.

The invention claimed is:

1. A cartridge, used by being set in a measuring device comprising a dispensing portion which comprises a pipette tip dispensing a reagent and/or a sample to each well on the cartridge, and automatically measuring a component in a sample, comprising:
    at least a heat-treatment well configured to perform heat treatment of the sample;
    a reaction well configured to produce a reaction between the component to be measured in the sample and a material specifically reacting therewith;
    a reagent-containing well containing a reagent required for measurement; and
    a diluting solution-containing well containing diluting solution for diluting the sample and/or a washing well containing washing solution for washing a reaction product produced by the reaction,
    wherein the reagent-containing well, the diluting solution-containing well, and/or the washing well is sealed with a seal,
    wherein information selected from the group consisting of information on a sample, information on an analyzing item, information on reagent management, and information on a calibration curve used for measurement is recorded on the seal, and wherein the record of the information is configured so as to be broken by breaking the seal with the leading end of the pipette tip when the cartridge is used.

2. The cartridge according to claim 1, wherein the information is recorded with a bar code.

3. The cartridge according to claim 1, wherein the seal is an aluminum laminate foil or a plastic film.

4. The cartridge according to claim 1, wherein the reagent-containing well contains a labeled antibody solution or a magnetic particle solution, and the depth of the reagent-containing well is smaller than the depth of the diluting solution-containing well and/or the depth of the washing well.

5. The cartridge according to claim 4, wherein the depth of the labeled antibody solution and/or the depth of the magnetic particle solution is smaller than the depth of the diluting solution and/or the depth of the washing solution.

6. A cartridge, used by being set in a device comprising a perforating mechanism, and automatically measuring a component in a sample, comprising:
   at least a heat-treatment well configured to perform heat treatment of the sample;
   a reaction well configured to produce a reaction between the component to be measured in the sample and a material specifically reacting therewith;
   a reagent-containing well containing a reagent required for measurement; and
   a diluting solution-containing well containing diluting solution for diluting the sample and/or a washing well containing washing solution for washing a reaction product produced by the reaction,
   wherein the reagent-containing well, the diluting solution-containing well, and/or the washing well is sealed with a seal,
   wherein information selected from the group consisting of information on a sample, information on an analyzing item, information on reagent management, and information on a calibration curve used for measurement is recorded on the seal, and
   wherein the record of the information is configured so as to be broken by breaking the seal with the perforating mechanism when the cartridge is used.

7. The cartridge according to claim 6, wherein the information is recorded with a bar code.

8. The cartridge according to claim 6, wherein the seal is an aluminum laminate foil or a plastic film.

9. The cartridge according to claim 6, wherein the reagent-containing well contains a labeled antibody solution or a magnetic particle solution, and the depth of the reagent-containing well is smaller than the depth of the diluting solution-containing well and/or the depth of the washing well.

10. The cartridge according to claim 9, wherein the depth of the labeled antibody solution and/or the depth of the magnetic particle solution is smaller than the depth of the diluting solution and/or the depth of the washing solution.

11. A method measuring a component in a sample using the cartridge of claim 1, and a measuring device comprising at least a cartridge-accommodating portion configured to accommodate the cartridge, a dispensing portion configured to dispense the reagent and/or the sample to each well on the cartridge accommodated in the cartridge-accommodating portion wherein the dispensing portion comprises a pipette tip, a measuring portion configured to measure a reaction product on the cartridge accommodated in the cartridge-accommodating portion, and a temperature controlling portion capable of controlling at least the heat-treatment well and the reaction well on the cartridge to desired temperatures comprising:
   breaking the record of the information by breaking the seal with the leading end of the pipette tip when the cartridge is used.

12. The method according to claim 11, wherein the information is recorded with a bar code, wherein the measuring device further comprises a barcode recognizing mechanism, and the method further comprises:
   recognizing the barcode by the barcode recognizing mechanism; and
   subsequently breaking the record of the information on barcode by breaking the seal with the leading end of the tip.

13. A method measuring a component in a sample using the cartridge of claim 6, and a measuring device comprising at least a cartridge-accommodating portion configured to accommodate the cartridge, a dispensing portion configured to dispense the reagent and/or the sample to each well on the cartridge accommodated in the cartridge-accommodating portion, a measuring portion configured to measure a reaction product on the cartridge accommodated in the cartridge-accommodating portion, a temperature controlling portion capable of controlling at least the heat-treatment well and the reaction well on the cartridge to desired temperatures, and a perforating mechanism for perforating the seal, the method comprising:
   breaking the record of the information by breaking the seal with the perforating mechanism when the cartridge is used.

14. The method according to claim 13, wherein the information is recorded with a bar code, wherein the measuring device further comprises a barcode recognizing mechanism, and the method further comprises:
   recognizing the barcode by the barcode recognizing mechanism; and
   subsequently breaking the record of the information on the barcode by breaking the seal with the perforating mechanism.

* * * * *